United States Patent [19]
Keppeler et al.

[11] Patent Number: 5,147,960

[45] Date of Patent: Sep. 15, 1992

[54] HETEROFUNCTIONAL DIOLS AND POLYURETHANE ELASTOMERS MANUFACTURED THEREFROM

[76] Inventors: Uwe Keppeler, 22 Ungsteiner Strasse, 6700 Ludwigshafen; Michael Bobrich, 3 In den Muehlgaerten, 6737 Boehl-Iggelheim, both of Fed. Rep. of Germany

[21] Appl. No.: 561,612

[22] Filed: Aug. 2, 1990

[30] Foreign Application Priority Data

Aug. 22, 1989 [JP] Japan ............................ 3927630

[51] Int. Cl.$^5$ ............................................ C08G 18/67
[52] U.S. Cl. ................................. 528/75; 549/551; 560/157; 560/159; 560/160; 560/165; 560/166
[58] Field of Search ........... 549/551, 157, 159, 160, 549/165, 166

[56] References Cited

U.S. PATENT DOCUMENTS

Re. 30,530  2/1981  Hopwood ..................... 560/165

Primary Examiner—Maurice J. Welsh
Assistant Examiner—Rachel Johnson
Attorney, Agent, or Firm—Keil & Weinkauf

[57] ABSTRACT

The invention relates to heterofunctional diols of formula I and to polyurethane elastomers prepared therefrom.

1 Claim, No Drawings

HETEROFUNCTIONAL DIOLS AND POLYURETHANE ELASTOMERS MANUFACTURED THEREFROM

The present invention relates to heterofunctional diols and polyurethane elastomers manufactured therefrom.

The use of diols for the preparation of condensation and addition polymers, such as polyesters or polyurethanes, which are preferably used in coating compositions, is well known. The need for coating compositions for special fields of application and having preselected properties calls for special components for their manufacture.

It is thus an object of the present invention to provide diols which are useful for the preparation of condensation and addition polymers, for example polyester or polyurethane elastomers containing functionalized side chains. The presence of functional groups leads to polymers having special characteristics, e.g. radiation curability, good pigment adhesion or low surface tension.

We have now found that this object can be achieved with a heterofunctional R' radical of formula I

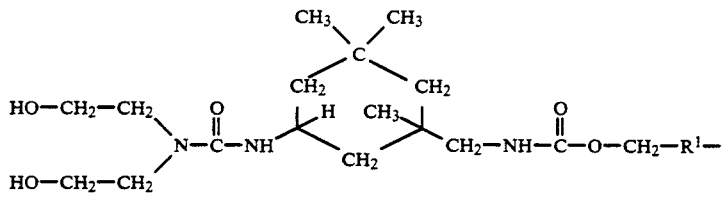

in which

R$^1$ is a straight-chain or branched-chain or cyclic radical having from 1 to 40 carbon atoms, the weight of said carbon atoms being from 20 to 86% of the weight of the diol, and X stands for an organic radical having at least one heterofunctional group selected from the group consisting of

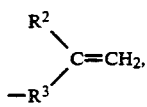

(in which R$^2$ is H or CH$_3$ and R$^3$ is O, —O—CH$_2$—or

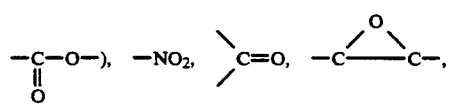

tertiary or quaternary amine and
—SO$_3$M, —OSO$_3$M, —COOM and

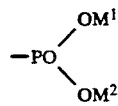

in which M stands for H, Li, Na, K or ammonium and M$^1$ and M$^2$ are the same or different and stand for H, Li, Na, K or alkyl.

The present invention also relates to polyurethane elastomers which exhibit side chains and are prepared by reacting A) a polydiol having a molecular weight between 400 and 10,000,
B) a mixture of at least two diols and, optionally,
C) a triol or polyol containing from 3 to 10 carbon atoms with D) a diisocyanate containing from 2 to 16 carbon atoms and, optionally,
E) an aminoalcohol containing from 2 to 16 carbon atoms, wherein the component B is a mixture of at least one straight-chain aliphatic diol (B1) containing from 2 to 10 carbon atoms and a diol (B2) of formula I, which is present therein in an amount of from 0.1 to 50% molar, based on the total component B.

The preparation of the heterofunctional diols of formula I of the invention is effected via a two-stage reaction known per se. In the fist stage, an alcohol of formula II $$HO-CH_2-R^1-X \qquad (II),$$

in which R$^1$ and X have the meanings stated above, is reacted with the more reactive group of isophorone diisocyanate at a temperature of from 10° to 60° C. optionally with the use of a catalyst. The second isocyanate group is then reacted with diethanolamine without previously isolating the intermediate. The reaction may be carried out without the use of a solvent but can, if necessary, be effected in a solvent, preferably tetrahydrofuran.

These diols of the invention may be used for the preparation of polyurethane elastomers, particularly those having a comb-like structure, which, depending on the functional group contained therein, are distinguished by special properties such as radiation curability, good pigment adhesion or low surface tension, and which provide highly elastic surface coatings which adhere well to a variety of substrates.

The polyurethanes of the invention may be manufactured by generally known methods with or without the use of solvents. When they are to be used as surface coating compositions, it is preferred to prepare them in solution, optionally in the presence of catalysts and other auxiliaries and/or additives. In this case, the reaction will be stopped in known manner by adding an excess of a primary and/or secondary monoamine (component E) when the desired end viscosity has been reached, as disclosed, for example, in DE-A 2,500,921.

When prepared in solution, the comb-like structure of the polymers is particularly advantageous, since it inhibits the formation of hydrogen bridges between individual polymer chains, which in turn improves the solubility of the products.

The component A (polydiol) used is a polyesterol, polyetherol or polycarbonate having a molecular weight of from 400 to 4000, preferably from 700 to 2,500. Advantageously, the polydiols are predominantly linear polymers having two terminal OH-groups. The acid number of the polydiols is less than 10 and preferably less than 3. The polyesterols may be prepared in a simple manner by esterifying aliphatic or aromatic dicarboxylic acids containing from 4 to 15, preferably 4 to 8, carbon atoms with aliphatic or cycloaliphatic glycols preferably containing from 2 to 20 carbon atoms or by polymerization of lactones containing from 3 to 10 carbon atoms. Examples of suitable dicarboxylic acids are glutaric, pimelic, suberic, sebacic, dodecanoic, isophthalic and, preferably, adipic, succinic and terephthalic acids. The dicarboxylic acids may be used singly or as a mixture. It may be advantageous, when preparing the polyesterols, to replace the dicarboxylic acids by the corresponding acid derivatives, such as carboxylic anhydrides or carboxylic chlorides. Examples of suitable glycols are diethylene glycol, pentanediol, decanediol-1,10 and 2,2,4-trimethylpentanediol-1,5. The preferred compounds are ethanediol-1,2, butanediol-1,5, hexanediol-1,6 and 2,2-dimethylpropanediol-1,3, 1,4-dimethylolcyclohexane, 1,4-diethanolcyclohexane and 1,4-diethanolpropane. Depending on the desired properties of the polyurethanes, the polyols may be used singly or as a mixture of various proportions. Suitable lactones for the preparation of the polyesterols are, for example, α, α-dimethyl-β-propiolactone, butyrolactone and, preferably, caprolactone. Examples of polyetherols are polytetrahydrofuran and polypropylene oxide diol. The polycarbonates are generally based on hexanediol-1,6.

The component B1 comprises straight-chain aliphatic diols containing from 2 to 10 carbon atoms and preferably from 2 to 6 carbon atoms, such as ethanediol-1,2, propanediol-1,3, butanediol-1,4, hexanediol-1,6, pentanediol-1,5, decanediol-1,10, 2-methyl-1,3-propanediol, 2-methyl-2-butyl-1,3-propanediol, 2,2-dimethyl-1,4-butanediol, 2-methyl-2-butyl-1,3-propanediol, neopentylglycol hydroxypivalate, diethylene glycol, triethylene glycol and methyldiethanolamine, 1,4-dimethylolcyclohexane and 1,4-diethanolcyclohexane. These diols may be used singly or as a mixture.

The component B2 comprises the diols of formula I of the invention. The proportion thereof in the total component B is from 0.1 to 50%, preferably from 1 to 30%, molar.

The triols (component C) used are compounds containing from 3 to 10, preferably 3 to 6, carbon atoms. Examples of suitable triols are glycerol and trimethylolpropane. Also suitable are low molecular weight reaction products of, for example, trimethylolpropane with ethylene oxide and/or propylene oxide. The presence of triols during polyaddition leads to branching of the final product and this has a positive effect on the mechanical properties of the polyurethane, provided no local cross-linkage occurs.

Examples of suitable polyols (component C) are erythritol, pentaerythriotol and sorbitol.

To form the NCO-group-containing intermediates, the components designated A, B and C above are reacted with aliphatic, cycloaliphatic or aromatic diisocyanates containing from 6 to 30 carbon atoms (component D). Suitable compounds for this purpose are, for example, toluylene-2,4-diisocyanate, m-phenylene diisocyanate, 4-chloro-1,3-phenylene diisocyanate, 1,5-naphthylene diisocyanate, 1,6-hexanemethylene diisocyanate, 1,4-cyclohexylene diisocyanate and 1,5-tetrahydronaphthylene diisocynate, diphenylmethane diisocyanate, dicyclohexylmethane diisocyanate or isophorone diisocyanate.

To form polyurethane having OH-group-containing urea groups at the chain ends, the NCO-group-containing intermediate from A to D is reacted with amino alcohols (component E). Such amino alcohols, which contain 2 to 16, preferably 3 to 6, carbon atoms, are, for example, monoethanolamine, methylisopropanolamine, ethylisopropanolamine, methylethanolamine, 3-aminopropanol, 1-ethylaminobutanol-2, 4-methyl-4-aminopentanol-2 and N-(2-hydroxyethyl)aniline. Diolamines are particularly suitable, since their addition to the chain end doubles the OH number of the polymer. Diethanolamine and diisopropanoldiamine are particularly useful.

The ratio of the components A to D to each other can be varied from 1.35 moles to 13 moles of diisocyanate, from 0.3 mole to 10 moles of diol containing from 2 to 20 carbon atoms and from 0.05 to 0.5 mole of triol, per mole of polydiol. The amount of diol used partly depends on the molecular weight of the polydiol used. However, it is advantageous, for practical reasons, to use an excess of diisocyanate of 3% more than the amount required for complete conversion of the reactants, so that the ratio of the number of hydroxyl groups used to the number of isocyanate groups in the reaction mixture is from 1.03 to 1.3 and preferably from 1.05 to 1.15. The excess of NCO-groups is then reacted stoichiometrically with the NH-groups of the amino alcohol, so that the ratio of the components (A–C):D:E is 1:(1.03–1.3):(0.03–0.3) and preferably 1:(1.05–1.15):(0.05–0.15).

The two-stage process can be effected in two different ways depending on the reaction conditions (amount of solvent, heat of reaction).

Method 1. The diisocyanate is placed in the reactor together with a small amount of solvent, and the components A, B and C and any catalyst, auxiliaries and additives are added in solution at a temperature of from 20° to 90° C. over a period of from 0.2 to 5 hours. The components are reacted to the desired NCO content, followed, in the second stage, by the addition of component E.

Method 2. In this procedure all of the starting components A to D are dissolved in a portion of the solvent to give a solution with a solids content of from 15–50% by weight. The solution is then stirred and, after the addition of catalyst, if any, heated to a temperature of from 20° to 90° C., preferably from 30° to 70° C. The components are then reacted to the desired NCO content, whereafter, in the second stage, component E is added.

In this two-stage process an NCO excess over components A–C is used in the first stage. In both methods it is possible to commence the reaction in part of the total solvent and to add the remaining solvent during or after the reaction.

Suitable solvents for use in the preparation of our polyurethanes are, preferably, cyclic ethers such as tetrahydrofuran and dioxane, and cyclic ketones such as cyclohexanone. Depending on their intended field of application, the polyurethanes may, of course, be dissolved in other strongly polar solvents, for example dimethyl formamide, N-methyl pyrrolidone, dimethyl sulfoxide or ethyleneglycol acetate. Similarly, it is possible to mix the said solvents with aromatics such as toluene or xylene and esters such as ethyl and butyl acetates.

Suitable catalysts for use in the preparation of the polyurethane and in the cross-linking reaction are, for example, tertiary amines such as triethylamine, triethylenediamine, N-methyl-pyridine and N-methyl-morpholine, metal salts such as tin octoate, lead octoate and zinc stearate, and organic metal compounds such as dibutyltin laurate. The amount of catalyst to be used depends on its activity. Generally, it is advantageous to use from 0.005 to 0.3, and preferably from 0.01 to 0.1, parts by weight of catalyst per 100 parts by weight of polyurethane.

The invention is illustrated below with reference to Examples.

EXAMPLES 1

222 Parts of isophorone diisocyanate were dissolved in 443 parts of tetrahydrofuran, and dibutyltin dilaurate was added as catalyst. There were then added, dropwise at 60° C., 116 parts of hydroxyethyl acrylate. On reaching the theoretical NCO content, 105 parts of diethanolamine were added with cooling under ice. A clear 50% solution was obtained. The IR spectrum indicates complete conversion of the NCO groups. The purity of the product was sufficient for further processing.

EXAMPLE 2

Example 1 was repeated except that 564 parts of 1H, 1H, 2H, 2H,-perfluoro-1-dodecanol were used in place of the hydroxy acrylate and the reaction was carried out in 891 parts of tetrahydrofuran.

EXAMPLE 3

Example 1 was repeated except at 270.5 parts of stearyl alcohol were used in place of the hydroxy acrylate and the reaction was carried out in 597.5 parts of tetrahydrofuran.

EXAMPLE 4

Example 1 was repeated except that 88 parts of hydroxybutanone-2 were used in place of the hydroxy acrylate and the reaction was carried out in 31 parts of tetrahydrofuran.

EXAMPLE 5

Example 1 was repeated except that 1,400 parts of the polyether monosulfonate Tegomer ® HS-3127 (Th. Goldschmidt AG) were used in place of the hydroxy acrylate and the reaction was carried out in 1,727 parts of tetrahydrofuran.

EXAMPLE 6

In a heated reaction vessel equipped with stirrer and reflux condenser, 210 parts of a polyester obtained from adipic acid and 1,4-butanediol (mol. wt. 1,000), 5.85 parts of 1,4-butanediol, 1.34 parts of trimethylolpropane, 88.6 parts of the diol used in Example 1, 131.25 parts of 4,4'-diphenylmethane diisocyanate were dissolved in 1,311.12 parts of tetrahydrofuran and heated to 55° C. The components were reacted to an end viscosity of 20 Pas (at 60° C.) and then diluted with 1,769.5 parts of tetrahydrofuran to a solids content of 12.5%. At the same time, the reaction was terminated by adding 3.85 parts of diethanolamine. The K value of the resulting polymer is 56.4, as measured in 1% solution in dimethyl formamide. Surface coatings produced with this composition can be cured by UV radiation or electron emission.

EXAMPLE 7

In a heated reaction vessel equipped with stirrer and reflux condenser, 200 parts of a polyester obtained from adipic acid and 1,4-butanediol (mol. wt. 1,000), 22.95 parts of 1,4-butanediol, 1.34 parts of trimethylolpropane, 51.81 parts of the diol used in Example 5, 131.25 parts of 4,4'-diphenylmethane diisocyanate were dissolved in 1,222.05 parts of tetrahydrofuran and heated to 55° C. The components were reacted to an end viscosity of 20 Pas (at 60° C.) and then diluted with 1,629.4 parts of tetrahydrofuran to a solids content of 12.5%. At the same time, the reaction was terminated by adding 3.85 parts of diethanolamine. The K value of the resulting polymer is 58, as measured in 1% solution in dimethyl formamide. Surface coatings obtained from this solution by a pouring technique showed good adhesion and a high degree of elasticity.

We claim:

1. A diol of the formula

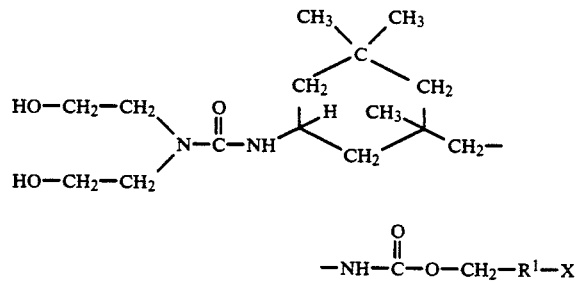

in which
R$^1$ is a straight-chain or branched-chain or cyclic radical having from 1 to 40 carbon atoms, the weight of the carbon atoms being from 20 to 86% of the weight of the R$^1$ radical;
X is a radical selected form the group consisting of

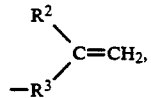

—NO$_2$; tertiary amine, quaternary amine, —SO$_3$M, —OSO$_3$M, —COOM and

wherein
R$^2$ is H or CH$_3$;
R$^3$ is —O—, —O—CH$_2$—or

M is H, Li Na K or ammonium; and M$^1$ and M$^2$ are the same or different and stand for H, Li, K or alkyl.

* * * * *